United States Patent [19]

Vincent et al.

[11] Patent Number: 5,262,155
[45] Date of Patent: Nov. 16, 1993

[54] GLYCEROL FUNCTIONAL POLYSILOXANES

[75] Inventors: Anne M. Vincent, Les Bons Villers; Audrey A. Wilson, Rixensart; Alan Zombeck, Lasne, all of Belgium

[73] Assignee: Dow Corning S.A., Seneffe, Belgium

[21] Appl. No.: 28,707

[22] Filed: Mar. 5, 1993

Related U.S. Application Data

[62] Division of Ser. No. 913,578, Jul. 15, 1992.

[51] Int. Cl.$^5$ .................... A61K 31/765; C08G 77/14
[52] U.S. Cl. ............................ 424/78.02; 424/78.03; 514/63; 528/29; 528/31; 528/15
[58] Field of Search ............ 514/63; 424/78.02, 78.03; 528/29, 31, 15

[56] References Cited

U.S. PATENT DOCUMENTS

| | | | |
|---|---|---|---|
| 2,846,458 | 8/1958 | Haluska | 260/448.2 |
| 4,504,313 | 3/1985 | Robertson | 106/38.2 |
| 4,772,592 | 9/1988 | Benzoni | 514/63 |
| 4,931,492 | 6/1990 | Foster et al. | 524/188 |
| 5,043,359 | 8/1991 | Ward et al. | 514/772 |
| 5,179,142 | 1/1993 | Ono et al. | 524/35 |

FOREIGN PATENT DOCUMENTS 59-039808A 3/1984 Japan.

*Primary Examiner*—John C. Bleutge
*Assistant Examiner*—M. W. Glass
*Attorney, Agent, or Firm*—James L. DeCesare

[57] ABSTRACT

A glycerol functional polysiloxane having the formula

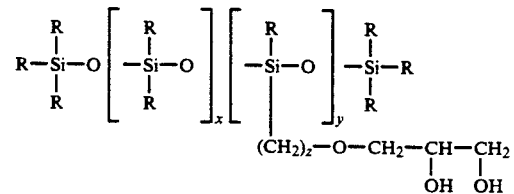

wherein R is an alkyl group having from one to six carbon atoms or a phenyl group; x has a value of from zero to about six hundred; y has a value of from one to about six hundred and z has a value of from two to about eight.

9 Claims, No Drawings

GLYCEROL FUNCTIONAL POLYSILOXANES

This is a divisional of copending application Ser. No. 07/913,578 filed on Jul. 15, 1992.

BACKGROUND OF THE INVENTION

This invention relates to personal care and more particularly to certain glycerol functional polysiloxanes useful as humectants in skin care applications.

The water content of the outer layers of the stratum corneum of the human epidermis is a controlling factor in the appearance of dry skin symptoms. When the stratum corneum contains an adequate amount of water within the range of about 10 to 20 percent, the skin remains flexible. However, when the water content falls below about ten percent, the stratum corneum often becomes brittle and rough and can exhibit scaling and cracking.

The stratum corneum receives its water from the deep layers of the epidermis by diffusion or when it is brought into direct contact with water. The diffusion process is controlled by the water content of the skin as well as by the concentration gradient. In a very dry environment for example, the water loss from the external skin layers can be significant and often exceeds the rate of replenishment by the diffusion process.

It is not uncommon therefore to include in skin conditioning compositions a humectant which is capable of introducing moisture to the skin from the atmosphere in conditions of moderate or high humidity. In conditions of low humidity humectants attract moisture from the lower layers of the skin. Humectants are materials which are hygroscopic and are therefore capable of retaining moisture. Among the most well known water retentive humectants capable of preventing drying out of the skin is glycerol. Glycerol is known to be an effective humectant and is generally considered harmless in cosmetic applications. It is a clear water white viscous liquid having the chemical formula $HOCH_2CHOHCH_2OH$. However, glycerol exhibits no bonding to the skin and hence is not durable or substantive with the result that it can be washed from the skin surface. It is used in many creams and lotions for the purpose of keeping the skin soft and for replacing skin moisture.

The prior art is replete with various formulations which contain glycerol as an ingredient. One such prior art composition is described in U.S. patent application Ser. No. 07/489117 filed Mar. 5, 1990 of Andrew H. Ward entitled "Glyceroxyfunctional Organosilicon Compounds", which application is assigned to Dow Corning Corporation. The Ward application which is now U.S. Pat. No. 5,043,359 issued Aug. 27, 1991, discloses a silicone compound having the group $-OCH_2CH(OH)CH_2OH$ directly bonded to a silicone atom in the polymer main chain. Upon contact with water, the silicone compound undergoes hydrolysis with the result that the Si—O bond is cleaved and free glycerol is released onto the skin accompanied by the simultaneous formation of silanol groups. However, as already noted, glycerol is not durable and can be easily removed from the skin surface by washing.

SUMMARY OF THE INVENTION

In accordance with the present invention, there are provided silicone compounds in which there is directly bonded to a silicone atom in the main chain of the polymer the group $-(CH_2)_zOCH_2CH(OH)CH_2OH$. These compounds differ from the compounds disclosed by the Ward application in the presence of the intervening spacer group $-(CH_2)_z-$. Because the Si—C bond is not broken by water there is no hydrolysis to free glycerol as in the Ward application. Rather, the compounds of the present invention are durable and skin substantive which is an advantage over the prior art as represented by the Ward application. Because of this advantage of durability and substantivity, the compounds of the present invention provide the benefit of longer lasting moisturisation and exhibit humectant characteristics of attracting water because of the presence in the molecule of the glycerol functionality. The silicone portion of the molecule contributes its benefits of skin softening, film forming and the facilitation of spreading of the composition over the skin surfaces.

DETAILED DESCRIPTION OF THE INVENTION

The present invention relates to new and novel compounds which are glycerol functional polysiloxanes having the formula

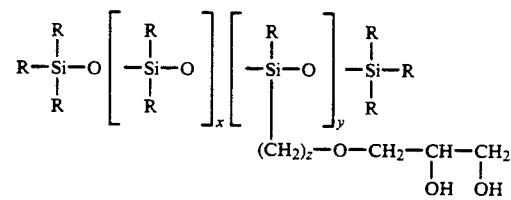

wherein R is an alkyl group having from one to six carbon atoms or a phenyl group; x has a value of from zero to six hundred; y has a value of from one to six hundred and z has a value of from two to eight. While x can be 0 to 600 x preferably has a value of from one to three hundred. More preferably x has a value of from one to one hundred, and more particularly x has a value of from forty-five to one hundred. While y can be 1 to 600, preferably y has a value of from one to 100 and more preferably 1 to 50. While z can be 2 to 8 preferably z has a value of from three to six. In the most preferred embodiment of the present invention R is methyl; x has a value of 45 to 98; y has a value of 1 to 10 and z is three.

While the compounds of the present invention can be used for direct application to the skin, it is preferred to include them as an ingredient in topical skin conditioning formulations. The glycerol functional polysiloxanes may be present in the skin conditioning formulation in an amount of about one to five percent by weight, and the compounds are particularly suitable for use in skin conditioning compositions which are in the form of creams although the compounds are equally effective in other delivered forms such as ointments, gels, lotions and emulsions.

The process for preparing the glycerol functional polysiloxanes of the present invention involves contacting alkenyloxy-1,2-propanediol with a polysiloxane having a reactive site. Preferably the alkenyloxy group is 3-allyloxy but other groups such as vinyloxy or 4-butenyloxy are also acceptable. The diol and the siloxane are preferably heated under nitrogen to about 75° C. in the presence of a solvent such as isopropanol. The reaction mixture may be catalysed with a noble metal catalyst such as chloroplatinic acid and allowed to reflux for thirty minutes. Any active metal catalyst is suitable for the reaction, and particularly preferred are platinum catalysts such as platinum acetylacetonate or chloroplatinic acid. The mixture may then be cooled and the solvent e.g. isopropanol removed under vacuum for example at about 110° C. The reaction mechanism as shown below has as reactive site R' hydrogen.

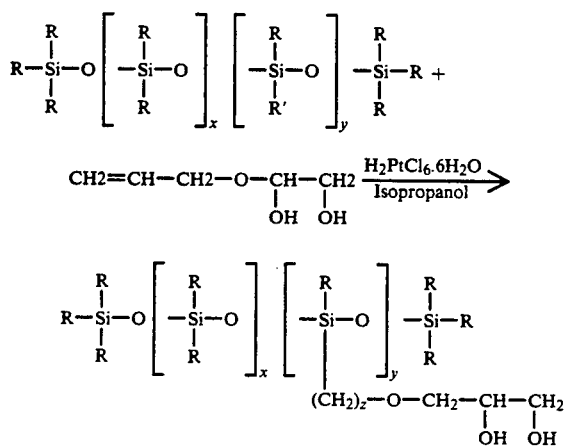

Following are examples illustrating the preparation of glycerol functional polysiloxanes according to the present invention.

EXAMPLE I

A mixture containing 16.43 weight percent of 3-allyloxy-1,2-propanediol, 58.47 weight percent of the siloxane $Me_3SiO(Me_2SiO)_{45}(MeHSiO)_5SiMe_3$, 0.2 percent by weight of sodium acetate and 24.75 weight percent of isopropanol, was heated to 75° C. under nitrogen. The mixture was catalysed with 0.15 weight percent of the catalyst $H_2PtCl_6$ in the form of a 0.7688 percent solution in isopropanol. The mixture was allowed to reflux for thirty minutes. The reaction mixture was allowed to cool and the isopropanol solvent was removed by the application of a vacuum of 50 mm/Hg and heating the mixture to 110° C. A product was isolated and identified as the glycerol functional polysiloxane $Me_3SiO(Me_2SiO)_{45}(MeRSiO)_5SiMe_3$ in which Me is methyl and R is the group $-CH_2CH_2CH_2-O-CH_2-CHOH-CH_2OH$.

EXAMPLE II

A mixture containing 9.57 weight percent of 3-allyloxy-1,2-propanediol, 65.17 weight percent of the siloxane $Me_3SiO(Me_2SiO)_{47.5}(MeHSiO)_{2.5}SiMe_3$, 0.2 percent by weight of sodium acetate and 24.91 weight percent of isopropanol, was heated to 75° C. under nitrogen. The mixture was catalysed with 0.15 weight percent of the catalyst $H_2PtCl_6$ in the form of a 0.7688 percent solution in isoproanol. The mixture was allowed to reflux for thirty minutes. The reaction mixture was allowed to cool and the isopropanol solvent was removed by the application of a vacuum of 50 mm/Hg and heating the mixture to 110° C. A product was isolated and identified as the glycerol functional polysiloxane $Me_3SiO(Me_2SiO)_{47.5}(MeRSiO)_{2.5}SiMe_3$ in which Me is methyl and R is the group $-CH_2CH_2CH_2-O-CH_2-CHOH-CH_2OH$.

EXAMPLE III

A mixture containing 4.39 weight percent of 3-allyloxy-1,2-propanediol, 70.35 weight percent of the siloxane $Me_3SiO(Me_2SiO)_{49}(MeHSiO)_1SiMe_3$, 0.2 percent by weight of sodium acetate and 24.91 weight percent of isopropanol, was heated to 75° C. under nitrogen. The mixture was catalysed with 0.15 weight percent of the catalyst $H_2PtCl_6$ in the form of a 0.7688 percent solution in isoproanol. The mixture was allowed to reflux for thirty minutes. The reaction mixture was allowed to cool and the isopropanol solvent was removed by the application of a vacuum of 50 mm/Hg and heating the mixture to 110° C. A product was isolated and identified as the glycerol functional polysiloxane $Me_3SiO(Me_2SiO)_{49}(MeRSiO)_1SiMe_3$ in which Me is methyl and R is the group $-CH_2CH_2CH_2-O-CH_2-CHOH-CH_2OH$.

EXAMPLE IV

A mixture containing 16.57 weight percent of 3-allyloxy-1,2-propanediol, 58.30 weight percent of the siloxane $Me_3SiO(Me_2SiO)_{90}(MeHSiO)_{10}SiMe_3$, 0.2 percent by weight of sodium acetate and 24.78 weight percent of isopropanol, was heated to 75° C. under nitrogen. The mixture was catalysed with 0.15 weight percent of the catalyst $H_2PtCl_6$ in the form of a 0.7688 percent solution in isoproanol. The mixture was allowed to reflux for thirty minutes. The reaction mixture was allowed to cool and the isopropanol solvent was removed by the application of a vacuum of 50 mm/Hg and heating the mixture to 110° C. A product was isolated and identified as the glycerol functional polysiloxane $Me_3SiO(Me_2SiO)_{90}(MeRSiO)_{10}SiMe_3$ in which Me is methyl and R is the group $-CH_2CH_2CH_2-O-CH_2-CHOH-CH_2OH$.

EXAMPLE V

A mixture containing 9.57 weight percent of 3-allyloxy-1,2-propanediol, 65.17 weight percent of the siloxane $Me_3SiO(Me_2SiO)_{95}(MeHSiO)_5SiMe_3$, 0.2 percent by weight of sodium acetate and 24.91 weight percent of isopropanol, was heated to 75° C. under nitrogen. The mixture was catalysed with 0.15 weight percent of the catalyst $H_2PtCl_6$ in the form of a 0.7688 percent solution in isoproanol. The mixture was allowed to reflux for thirty minutes. The reaction mixture was allowed to cool and the isopropanol solvent was removed by the application of a vacuum of 50 mm/Hg and heating the mixture to 110° C. A product was isolated and identified as the glycerol functional polysiloxane $Me_3SiO(Me_2SiO)_{95}(MeRSiO)_5SiMe_3$ in which Me is methyl and R is the group $-CH_2CH_2CH_2-O-CH_2-CHOH-CH_2OH$.

The polymerisation catalyst for the reaction can include a variety of hydrosilation catalysts known to promote the reaction of vinyl-functional radicals with silicon-bonded hydrogen atoms. Active metal catalysts such as platinum or rhodium-containing metal compound are included in this class of catalysts. Platinum catalysts such as platinum acetylacetonate or chloroplatinic acid are representative of these compounds and suitable for use. A preferred catalyst mixture is a chloroplatinic acid complex of divinyltetramethyldisiloxane diluted in dimethylvinylsiloxy endblocked polydimethylsiloxane which may be prepared according to methods described by Willing in U.S. Pat. No. 3,419,593. Most preferably this mixture contains about 0.6 weight percent platinum.

Hydrosilation catalysts are well known in the art and the interested reader is referred to the following patents for detailed descriptions regarding their preparation and use: Speier, U.S. Pat. No. 2,823,218; Willing, U.S. Pat. No. 3,419,359; Kookootsedes, U.S. Pat. No. 3,445,420; Polmanteer et al, U.S. Pat. No. 3,697,473; Nitzsche, U.S. Pat. No. 3,814,731; Chandra, U.S. Pat. No. 3,890,359 and Sandford, U.S. Pat. No. 4,123,604. Many of the catalysts known in the art require the reactants to be heated in order for reaction to occur. When such catalysts are employed this requirement must be taken into consideration.

When platinum catalysts are used an inhibitor may be required in order to improve the shelf life of the starting materials and to control the viscosity-time profile of the compositions. These inhibitors are also known in the art and include ethylenically unsaturated isocyanurates, such as trialkylisocyanurate, dialkylacetylenedicarboxylates, alkyl maleates, phosphines, phosphites, aminoalkyl silanes, sulphoxides, acrylonotrile derivatives and others. Particular inhibitors preferably used are diethyl fumarate, bis(2-methoxy-1-methylene)maleate, bis(2-methoxy-1-methylethyl)maleate and similar compounds.

The concentrations of catalyst and inhibitor to be used in the present invention may be determined by routine experimentation. Typically, the effective amount of catalyst should be in a range so as to provide from about 0.1 to 1000 parts per million (ppm) of platinum by weight in the compositions of the present invention. As an example, when the preferred catalyst mixture (i.e. the chloroplatinic acid complex of divinyltetramethyldisiloxane containing about 0.6% by weight of platinum) and inhibitor (i.e. bis(2-methoxy-1-methylethyl)-maleate) are employed, a ratio by weight of inhibitor to catalyst mixture ranging from zero to about 0.6 provides a suitably wide range of inhibition which is adequate under most practical conditions of manufacture.

The substantivity of the waxy glycerol functional polysiloxanes of the present invention was verified by the use of in vivo Fourier transform infrared spectroscopy with attenuated total reflectance (ATR/FTIR) in accordance with the procedure described in the *Journal of the Society of Cosmetic Chemists*, Volume 37, pages 73 to 89, March/April 1986. Test data indicated that the waxy glycerol functional polysiloxanes were capable of providing an occlusive film on the skin similar to petrolatum which enhances moisturisation of the skin.

It will be apparent from the foregoing that many other variations and modifications may be made in the compounds and compositions described herein without departing from the essential essence of the invention. It should be understood that the forms of the invention described herein are exemplary and not intended as limitations on the scope of the present invention as defined in the appended claims.

That which is claimed is:

1. A method of conditioning skin comprising topically applying to the skin a glycerol functional polysiloxane having the formula

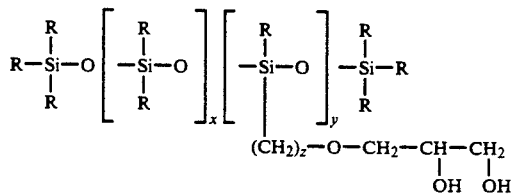

wherein R is an alkyl group having from one to six carbon atoms or a phenyl group; x has a value of from zero to about six hundred; y has a value of from one to about six hundred and z has a value of from two to about eight.

2. A method according to claim 1 in which R is methyl.

3. A method according to claim 1 in which x has a value of from one to three hundred.

4. A method according to claim 3 in which x has a value of from one to one hundred.

5. A method according to claim 4 in which x has a value of from forty-five to one hundred.

6. A method according to claim 1 in which y has a value of from one to one hundred.

7. A method according to claim 1 claims in which z has a value of from three to six.

8. A method according to claim 1 in which R is methyl; x has a value of 45–98; y has a value of 1 to 10 and z is three.

9. A method according to claim 1 in which one to five percent by weight of the glycerol functional polysiloxane is applied to the skin and rubbed into the skin.

* * * * *